2 Sheets—Sheet 1.

C. A. EISENHART.

ELECTRICAL APPARATUS FOR DENTAL OPERATIONS.

No. 10,907. Reissued Mar. 6, 1888.

WITNESSES

Edwin L. Yewell,

O. E. Duffy

INVENTOR

Chas. A. Eisenhart by Robt. H. Read.

his Attorney

N. PETERS, Photo-Lithographer, Washington, D. C.

C. A. EISENHART.

ELECTRICAL APPARATUS FOR DENTAL OPERATIONS.

No. 10,907. Reissued Mar. 6, 1888.

WITNESSES,

Edwin L. Yewell

O. E. Duffy

INVENTOR,

Chas. A. Eisenhart, by Robt. H. Read.

his Attorney

N. PETERS, Photo-Lithographer, Washington, D. C.

UNITED STATES PATENT OFFICE.

CHARLES A. EISENHART, OF YORK, PENNSYLVANIA.

ELECTRICAL APPARATUS FOR DENTAL OPERATIONS.

SPECIFICATION forming part of Reissued Letters Patent No. 10,907, dated March 6, 1888.

Original No. 331,121, dated November 24, 1885. Application for reissue filed January 24, 1888. Serial No. 261,802.

*To all whom it may concern:*

Be it known that I, CHARLES AUGUSTUS EISENHART, a citizen of the United States, residing at York, in the county of York and State of Pennsylvania, have invented certain new and useful Improved Electrical Apparatus for Dental Operations, of which the following is a full, clear, and exact description.

My invention relates to the class of apparatus shown in my application for patent, Serial No. 147,686, filed November 11, 1884; and it consists in certain features of construction, which will be hereinafter clearly indicated.

Figure 1:
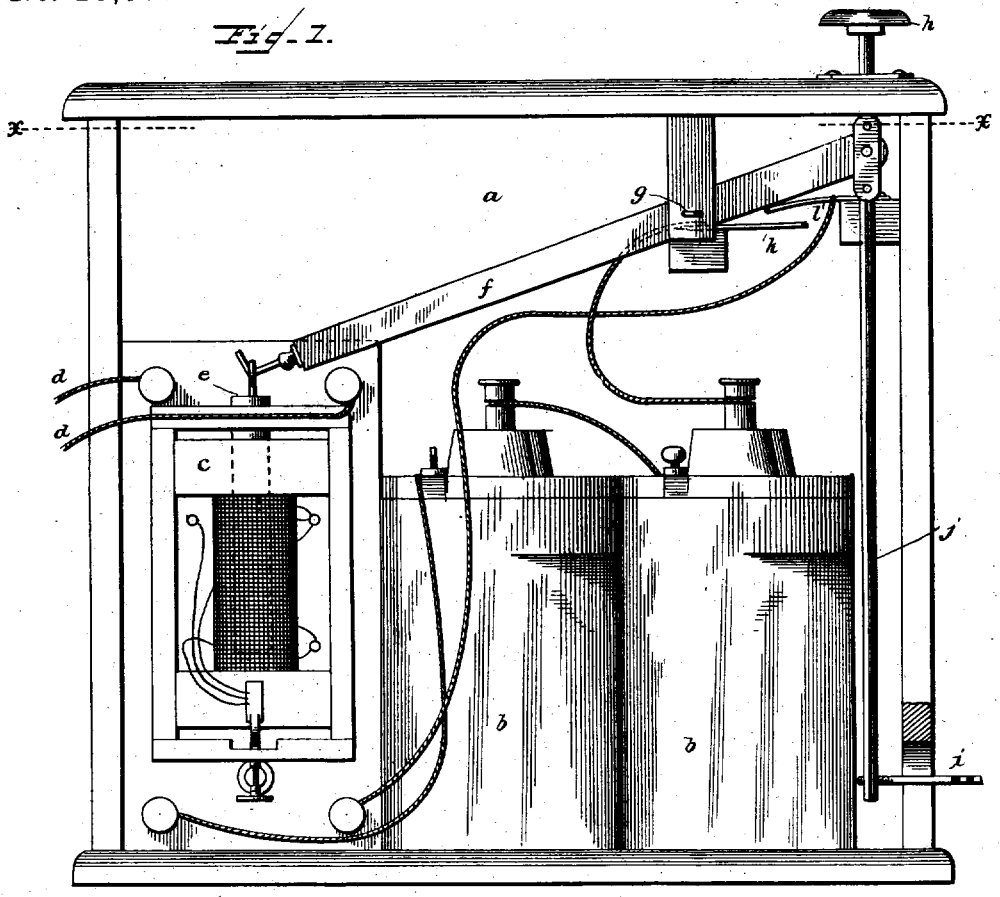
Figure 2:
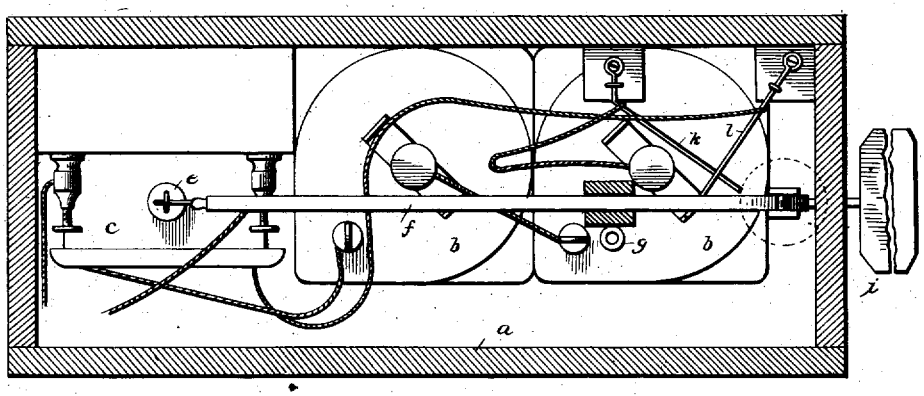
Figure 3:
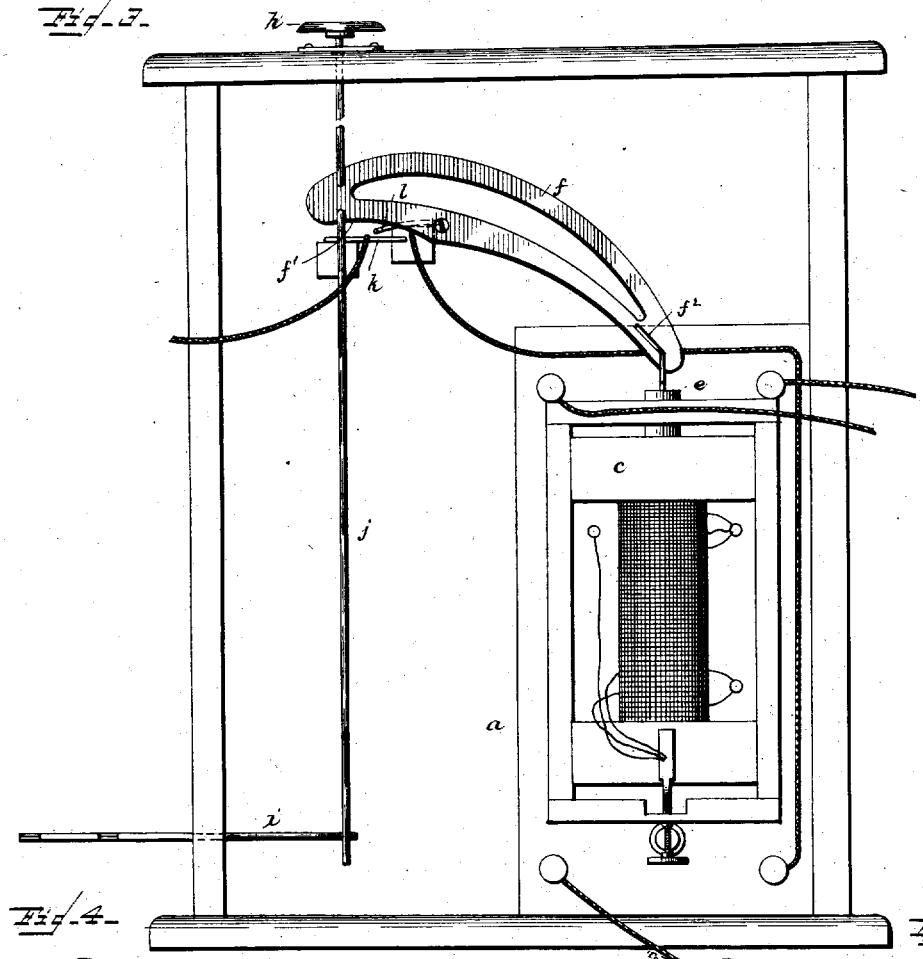
Figure 4:
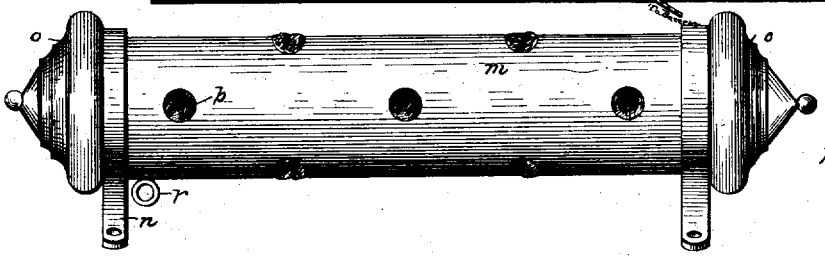
Figure 5:
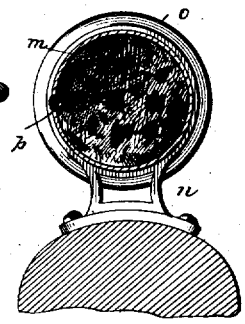

In the accompanying drawings, in the several figures of which like parts are similarly designated, Figure 1 is an elevation of my apparatus without the dischargers; Fig. 2, a top plan view of the same on line *x x*, Fig. 1. Fig. 3 is an elevation of a modification. Fig. 4 is a side view of one of the dischargers. Fig. 5 is a cross-section of the same on the line *y y*.

In order to render my apparatus easily portable, and at the same time get it within a small compass, I employ a box, *a*, containing, say, two cells (preferably Leclanche's) and an induction-coil, *c*, of any approved construction, suitably connected. From the coil conductors *d d* lead to the dischargers, such as shown in Figs. 4 and 5, or those shown in my application referred to. The sheath *e*, or regulator for the strength of the induced current, which is adapted to slide over the core of the induction-coil, in a manner well-known to constructors of such apparatus, and shown in dotted lines and partial side elevation, Fig. 1, and in plan, Fig. 2, is operated by a lever, *f*, loose-jointed thereto and pivoted, say at *g*, in hangers from the top of the box, which lever is actuated by a hand-piece, *h*, connected therewith and extending up out of the box, or by a pedal, *i*, connected with a rod, *j*, depending from the lever. The hand-piece and pedal are detachably connected with the lever, so as to be placed in the box when it is to be moved from place to place or packed away. The elements of the cell or cells (one or more of which may be used) are connected to contact-makers *k l*, one contact-maker, *k*, being connected with one element of one cell directly, and the other contact-maker being connected with the other element of the adjoining cell through the primary wire of the induction-coil, as clearly shown in Fig. 1. The contact-makers in this instance are pieces of wire arranged crosswise of and one above another beneath the short end of the lever *f*, and it will be seen that the depression of the lever *f* wipes the wire *l* across and in contact with the wire *k* and makes or closes the primary circuit. By arranging the contacts in this way, so that they will wipe or move across each other, their contact-surfaces are always kept bright and clean, and hence the certainty of their action insured; and I esteem this an essential feature of my invention, since it is specially useful where the metal is subject to oxidation or fouling in damp places.

In Fig. 3 I have shown a form of my apparatus in which the cells are omitted and may be placed in a cellar or elsewhere and connected to the induction-coil in suitable manner; and I have substituted for the lever, Figs. 1 and 2, a bell-crank lever, the lower portion of the short end of which is curved, as at $f'$, to act in conjunction with the contact-wires *k l*, and this curvature of the lever will still further increase the wiping action of one wire upon the other. The long end of the lever is slotted at $f^2$, to permit the rise and fall of the sheath as said lever is moved on its pivot.

It is obvious that the contact-wires might be crossed under the pedal and be operated by it where that form of operating mechanism alone is used. Instead of the hand-piece shown in my application referred to, I may omit from it the metal straps and have simply a concave plate to be applied to the arm of a chair in any suitable manner; but the hand-piece, or, technically, the "discharger" I prefer is composed of a metal or other electricity-conducting tube, *m*, Figs. 4 and 5, provided with posts *n*, whereby it may be secured to the top, side, or bottom of the arms of a dental or other chair or support, having its ends closed by detachable caps *o*, of a more or less ornamental character. Owing to the hardening of the skin of the hands and their consequent lack of susceptibility to electric influence, I prefer to provide a number of holes, *p*, in the tube *m*, and fill said tube with wet sponge or other water-absorbent, which will project through said holes, and, coming in contact with the hands, moisten and thereby soften them sufficiently to render them susceptible to the current. Electric connection is made with the dischargers by the post or eye *r*.

In use the patient grasps the dischargers or electrodes, and when the dentist is ready to operate he closes the primary circuit with his hand or foot. The high-tension current, passing through the muscles of the arms and body, acts in some way to neutralize the pain of the tooth nerves and alleviates in a marked degree the suffering of a patient during an operation.

It is obvious that a patient can be more or less electrified by the operator's entire control of the induction-coil.

What I claim is—

1. In a dental electric apparatus, the combination of an induction-coil, a regulator for varying the induced current, a circuit-closer in the primary circuit, a controlling device for operating the circuit-closer and regulator coincidently, an electric generator in the primary circuit, and suitable dischargers at the secondary terminals.

2. In a dental electric apparatus, the combination of a case, an electric generator, an induction-coil, dischargers in the secondary circuit, a circuit-closer in the primary circuit, and hand and foot pieces operating in conjunction with the circuit-closer to make and break the circuit.

3. In an electric apparatus for dental use, the tubular discharger provided with holes and containing a moistened substance, substantially as described.

4. The combination, in a dental electric apparatus, of the case, an electric generator, induction-coil, dischargers in the secondary circuit, a circuit-closer in the primary circuit, and a foot-piece acting in conjunction with the circuit-closer to make and break the circuit, substantially as described.

5. In a dental electric apparatus, the combination of an induction-coil, a primary circuit, including a circuit-changer accessible to the operator during a dental operation, and a secondary circuit provided with dischargers adapted to be grasped by the patient to pass the induced current through his body contemporaneously with said operation.

6. In a dental electric apparatus, the combination of an induction-coil, a primary circuit, a circuit-closer in said circuit accessible to the operator during an operation, a secondary circuit provided with terminals to pass the induced current through the patient's body, and means to vary the strength of the induced current.

In testimony whereof I have hereunto signed my name in the presence of two subscribing witnesses.

CHARLES A. EISENHART.

Witnesses:
M. P. CALLAN,
ROBT. H. READ.